(12) United States Patent
Gerlach et al.

(10) Patent No.: US 7,122,702 B2
(45) Date of Patent: Oct. 17, 2006

(54) CATALYTIC HYDROGENATION OF AN ALIPHATICALLY UNSATURATED GROUP IN AN ORGANIC COMPOUND

(75) Inventors: Till Gerlach, Ludwigshafen (DE); Frank Funke, Ludwigshafen (DE); Johann-Peter Melder, Böhl-Iggelheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/731,167

(22) Filed: Dec. 10, 2003

(65) Prior Publication Data
US 2004/0122265 A1    Jun. 24, 2004

(30) Foreign Application Priority Data
Dec. 20, 2002 (DE) .............................. 102 61 194

(51) Int. Cl.
C07C 209/26 (2006.01)
C07C 209/48 (2006.01)
(52) U.S. Cl. ................. 564/472; 564/480; 564/490
(58) Field of Classification Search ................. 568/861
See application file for complete search history.

(56) References Cited

U.S. PATENT DOCUMENTS

| 5,015,788 A |   | 5/1991  | Toussaint et al. |
| 5,037,793 A |   | 8/1991  | Toussaint et al. |
| 5,354,915 A | * | 10/1994 | Reichle ..................... 568/881 |
| 5,696,048 A |   | 12/1997 | Breitscheidel et al. |
| 6,034,029 A | * | 3/2000  | Wulff-Doring et al. ..... 502/308 |

FOREIGN PATENT DOCUMENTS

| EP | 394 841 | 10/1990 |
| EP | 394 842 | 10/1990 |
| EP | 742 045 | 11/1996 |

OTHER PUBLICATIONS

Hawley's Codensed Chemical Dictionary 13 ed., R. J. Lewis editor, Van Nostrand Reinhold, New York, NY, 1997, p. 32.*

* cited by examiner

*Primary Examiner*—Brian Davis
(74) *Attorney, Agent, or Firm*—Novak Druce & Quigg, LLP

(57) ABSTRACT

Process for the catalytic hydrogenation of an aliphatically unsaturated group in an organic compound in the presence of a catalyst whose preparation has involved precipitation of catalytically active components onto monoclinic, tetragonal or cubic zirconium dioxide.

15 Claims, 1 Drawing Sheet

Figure 1:
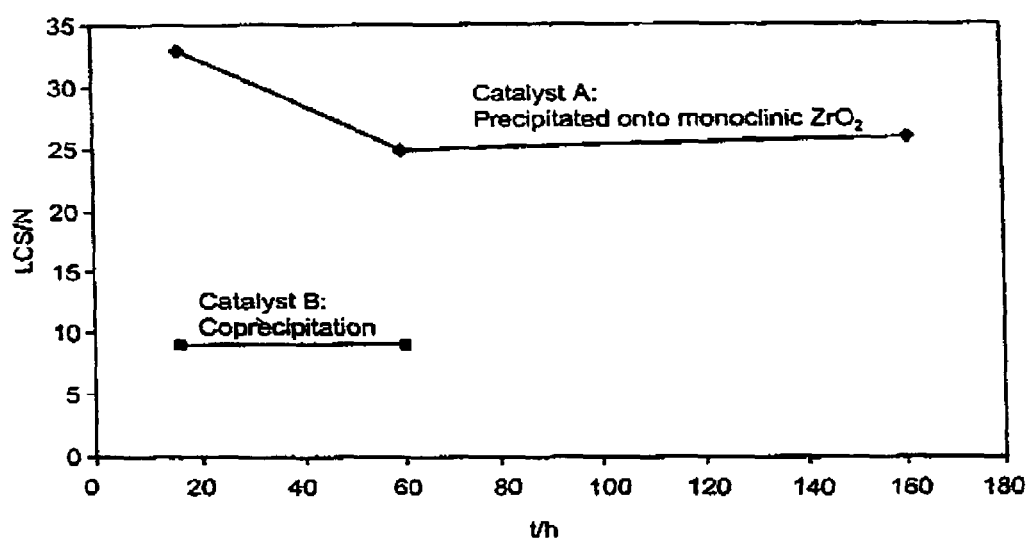

CATALYTIC HYDROGENATION OF AN ALIPHATICALLY UNSATURATED GROUP IN AN ORGANIC COMPOUND

The present invention relates to a process for the catalytic hydrogenation of an aliphatically unsaturated group in an organic compound.

EP-A1-394 841 and EP-A1-394 842 (both BASF AG) describe the use of catalysts comprising zirconium dioxide, copper and nickel in processes for the hydrogenation of aliphatic CC double bonds and CC triple bonds.

EP-A1-742 045 (BASF AG) relates to particular cobalt catalysts and their use in processes for the hydrogenation of organic nitriles and imines.

The catalysts of the prior art which comprise zirconium oxide are preferably obtainable by coprecipitation of water-soluble compounds of appropriate metals including zirconium by means of mineral bases and subsequent drying and heat treatment (cf., for example, EP-A1-394 842, column 2, lines 34 to 51).

However, in the abovementioned coprecipitation, part of the water-soluble zirconium salt can also be replaced by solid zirconium dioxide (cf., for example, EP-A1-394 842, column 2, line 52, to column 3, line 3)

A parallel German patent application (BASF AG) filed on the same day describes a process for preparing an amine by reacting a primary or secondary alcohol, aldehyde or ketone with hydrogen and a nitrogen compound selected from the group consisting of ammonia and primary and secondary amines in the presence of a catalyst using a catalyst whose preparation has involved precipitation of catalytically active components onto monoclinic, tetragonal or cubic zirconium dioxide.

A parallel German patent application (BASF AG) filed on the same day relates to a process for preparing a symmetrical secondary amine by reaction of a primary amine in the presence of hydrogen and a catalyst whose preparation has involved precipitation of catalytically active components onto monoclinic, tetragonal or cubic zirconium dioxide.

A disadvantage of the heterogeneous catalysts of the prior art which comprise zirconium dioxide in the hydrogenation of aliphatically unsaturated groups in organic compounds is, as has been recognized according to the present invention, the decrease in their mechanical stability under the reaction conditions under which they are used, in particular in the presence of reaction media comprising water. A consequence of less mechanically stable heterogeneous catalysts is the necessity of changing the catalyst in the reactor more frequently and thus a reduced space-time yield.

It is an object of the present invention to remedy the disadvantages of the prior art and to provide an improved process for the catalytic hydrogenation of an aliphatically unsaturated group in organic compounds using a catalyst having improved mechanical properties under the reaction conditions of its use and thus to improve the economics of previous processes, in particular those in which catalysts comprising zirconium dioxide are used.

According to the present invention, it has been recognized that a reason for the not fully satisfactory mechanical stability, i.e. the mechanical softening, of the known catalysts comprising zirconium dioxide under reaction conditions is the fact that, for example when the abovementioned (co)precipitation technique is employed, zirconium dioxide is initially present in wholly or partially amorphous form and under the conditions of the chemical reaction catalyzed by means of these catalysts undergoes a complete or partial crystallization, i.e. conversion of the modification into tetragonal, monoclinic or cubic zirconium dioxide. In hydrogenation reactions, the reaction conditions employed usually involve elevated temperature (e.g. 40–300° C.) and elevated pressure (e.g. 5–320 bar).

We have found that the use of zirconium dioxide which is in a modification which is thermodynamically stable or at least metastable under the reaction conditions of the hydrogenation reaction, e.g. monoclinic, tetragonal or cubic zirconium dioxide, in the preparation of a catalyst comprising zirconium dioxide significantly increases the mechanical stability of the resulting catalysts under the reaction conditions, particularly in the presence of reaction media comprising water.

The present invention accordingly provides a process for the catalytic hydrogenation of an aliphatically unsaturated group in an organic compound in the presence of a catalyst whose preparation has involved precipitation of catalytically active components onto monoclinic, tetragonal or cubic zirconium dioxide.

The catalytically active components precipitated on are, in particular, salts of metals selected from groups 8 to 11 (corresponding to transition groups VIII and IB) of the Periodic Table of the Elements, especially from the group consisting of Fe, Co, Ni, Ru, Rh, Pd, Pt and Cu. The metal is particularly preferably selected from the group consisting of Cu, Ni and Co.

In general, the catalysts in the process of the present invention are preferably used in the form of catalysts which consist entirely of catalytically active composition and possibly a shaping aid (e.g. graphite or stearic acid) if the catalyst is used as shaped bodies, i.e. contain no further catalytically inactive constituents.

The catalytically active composition can be introduced into the reaction vessel after milling as power or as cross material or, preferably, introduced into the reactor after milling, mixing with shaping aids, shaping and heat treatment as shaped catalyst bodies, for example as pellets, spheres, rings, extrudates (e.g. rods).

The abovementioned concentrations (in % by weight) of the components of the catalyst are based, unless indicated otherwise, on the catalytically active composition of the catalyst prepared before treatment with hydrogen.

The catalytically active composition of the catalyst is defined as the sum of the catalytically active constituents and the composition comprises, before treatment with hydrogen, essentially the catalytically active constituents monoclinic, tetragonal or cubic zirconium dioxide (or mixtures of these modifications) and metal salts as further catalytically active components.

The sum of the abovementioned catalytically active constituents, calculated in oxidic form, e.g. as $ZrO_2$, CuO, NiO and CoO, in the catalytically active composition before treatment with hydrogen is generally from 70 to 100% by weight, preferably from 80 to 100% by weight, particularly preferably from 90 to 100% by weight, in particular from 95 to 100% by weight, very particularly preferably from >98 to 100% by weight.

The catalytically active composition of the catalysts used in the process of the present invention can further comprise one or more elements (oxidation state 0), or inorganic or organic compounds thereof, selected from groups IA to VIA and IB to VIIB and VIII of the Periodic Table.

Examples of such elements and compounds thereof are:

Transition metals such as Mn and manganese oxides, Re and rhenium oxides, Cr and chromium oxides, Mo and molybdenum oxides, W and tungsten oxides, Ta and tantalum oxides, Nb and niobium oxides or niobium oxalate, V and vanadium oxides or vanadyl pyrophosphate, zinc and zinc oxides, silver and silver oxides, lanthanides such as Ce and $CeO_2$ or Pr and $Pr_2O_3$, alkali metal oxides such as $Na_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

The catalytically active composition of preferred catalysts for use in the process of the present invention comprises, before treatment with hydrogen, from 20 to 85% by weight, preferably from 20 to 65% by weight, particularly preferably from 22 to 40% by weight, of monoclinic, tetragonal or cubic zirconium dioxide ($ZrO_2$) (or mixtures of these modifications), from 1 to 30% by weight, particularly preferably from 2 to 25% by weight, of oxygen-containing compounds of copper, calculated as CuO, and from 14 to 70% by weight, preferably from 15 to 50% by weight, particularly preferably from 21 to 45% by weight, of oxygen-containing compounds of nickel, calculated as NiO, with the molar ratio of nickel to copper preferably being greater than 1, in particular greater than 1.2, very particularly preferably from 1.8 to 8.5.

The catalytically active composition of particularly preferred catalysts further comprises, before treatment with hydrogen, from 15 to 50% by weight, particularly preferably from 21 to 45% by weight, of oxygen-containing compounds of cobalt, calculated as CoO.

The oxygen-containing compounds of copper, nickel and, if applicable, cobalt, each calculated as CuO, NiO and CoO, of the preferred catalysts are generally present in the catalytically active composition (before treatment with hydrogen) in total amounts of from 15 to 80% by weight, preferably from 35 to 80% by weight, particularly preferably from 60 to 78% by weight, with the molar ratio of nickel to copper particularly preferably being greater than 1.

The catalysts used according to the present invention can be prepared as follows.

In the preparation of the catalysts, the term "precipitation onto" refers to a procedure in which a sparingly soluble support material is suspended in a liquid, usually water, the doping components are used as readily soluble compounds and are dissolved in a liquid, usually water, and are then precipitated onto the suspended support by addition of a precipitant (e.g. as described in EP-A1-394 842, columns 2–3; EP-A2-394 841, page 2, line 45, to page 3, line 2; and A. B. Stiles, Catalyst Manufacture, Marcel Dekker, Inc., 1983, page 15).

According to the present invention, the support material used for preparation of the catalyst is zirconium dioxide in a thermodynamically stable or metastable modification, i.e. in the monoclinic, tetragonal or cubic modification.

The basic properties of zirconium dioxide are summarized in K. Dyrek, A. Adamski, Z. Sojka, Ceramic Interfaces 2, University Press, Cambridge, 2001, pp. 241–259, including the monoclinic, tetragonal and cubic modifications which exist and their preparation.

The zirconium dioxide crystal structure can, particularly in the case of the tetragonal modification, be stabilized further by additions of one or more oxides of metals of transition group IIIB or main group IIA of the Periodic Table, in particular yttrium oxide, calcium oxide, lanthanum oxide, magnesium oxide or scandium oxide.

This stabilization effects, for example, total or partial inhibition of the conversion of the tetragonal modification into the most thermodynamically stable monoclinic modification.

To prepare the catalyst, the zirconium dioxide is suspended in a solvent, e.g. in water. The metal salts dissolved, for example, in water are then added and basic salts which are sparingly soluble or insoluble in the solvent used, e.g. water, are subsequently precipitated by addition of, for example, an alkali metal hydroxide.

The precipitates obtained in these precipitation reactions are generally not chemically uniform and usually comprise mixtures of oxides, hydrated oxides, hydroxides, carbonates and/or hydrogencarbonates of the metals used.

The precipitation can, for example, be carried out at 20–100° C., in particular 50–90° C., especially 60–80° C.

As an alternative, the metal salt solution and the alkali can be introduced simultaneously into a vessel in which the zirconium dioxide support suspension is present. The support can also be suspended in the metal salt solution and this can be introduced into a precipitation vessel simultaneously with the alkali.

The further catalyst preparation is then carried out by known methods, e.g. filtration, washing, drying, calcination, shaping, reduction/passivation.

The catalysts prepared in this way comprise, prior to reduction/passivation, the catalytically active metals in the form of a mixture of their oxygen-containing compounds, in particular as oxides and mixed oxides.

The catalysts can be stored as such after their preparation. Before use as catalysts for the catalytic hydrogenation of an aliphatically unsaturated group in an organic compound, they are usually prereduced by treatment with hydrogen. However, they can also be used without prereduction, in which case they are then reduced under the conditions of the hydrogenation reaction by the hydrogen present in the reactor. To carry out the prereduction, the catalysts are generally firstly exposed to a nitrogen/hydrogen atmosphere at from 150 to 200° C. for a period of from 12 to 20 hours and subsequently treated in a hydrogen atmosphere at from 200 to 400° C. for up to about 24 hours. In this prereduction, part of the oxygen-containing metal compounds present in the catalysts is reduced to the corresponding metals, so that these are present together with the various oxygen compounds in the active form of the catalyst.

In particular, the aliphatically unsaturated group in the organic compounds used in the process of the present invention is an aliphatic CC double bond or CN double bond, an aliphatic CC triple bond or CN triple bond or an aldehyde group or keto group.

For example, the hydrogenation of aliphatically unsaturated compounds of the formula I

(I)

and of the formula III

(III)

where $R^1$, $R^2$, $R^3$, $R^4$ are each hydrogen (H), alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkly, such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl or alkylheteroaryl such as $C_{4-20}$-alkyheteroaryl, and in the case of unsaturated compounds of the formula I $R^1$ and $R^2$ may also together form $(CH_2)_l$—$CH_2$—X—$(CH_2)_m$, or $R^2$ and $R^4$ may also together form $(CH_2)_l$—X—$(CH_2)_m$, where x is $CH_2$, $CHR^5$, oxygen (O), sulfur (S) or $NR^5$, $R^5$ is hydrogen (H), alkyl such as $C_{1-4}$-alkyl, alkylphenyl such as $C_{7-40}$-alkylphenyl, I, m are each an integer from 1 to 4, is of particular commercial interest.

For this reason, the hydrogenation process of the present invention is employed for preparing the compounds II (from I) and IV and V (from III), where $R^1$, $R^2$, $R^3$ and $R^4$ are as defined above.

$$R^1\underset{H}{\overset{}{C}}-\underset{H}{\overset{R^3}{C}}R^4 \quad (II)$$

$$R^1-\underset{H}{C}=\underset{H}{C}-R^2 \quad (IV)$$

$$R^1-\underset{H_2}{C}-\underset{H_2}{C}-R^2 \quad (V)$$

The process of the present invention is also of particular commercial interest for, for example, the hydrogenation of nitriles of the formula VI $$R^1-\equiv N, \quad (VI)$$

where $R^1$ is alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{2-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl or alkylheteroaryl such as $C_{4-20}$-alkylheteroaryl, to form the corresponding primary amines VII $$R^1-CH_2NH_2 \quad (VII)$$

Futhermore, the process of the present invention is also of particular commercial interest for the hydrogenation of aldehydes or aldimines of the formula VIIIa or VIIIb $$R^1-CHO \quad (VIIIa)$$

$$R^1-CH=NH \quad (VIIIb)$$

where $R^1$ is hydrogen (H), alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl or alkylheteroaryl such as $C_{4-20}$-alkylheteroaryl, to form the corresponding primary alcohols IXa or primary amines IXb $$R^1-CH_2OH \quad (IXa),$$

$$R^1-CH_2NH_2 \quad (IXb).$$

In addition, the process of the present invention is also of particular commercial interest for the hydrogenation of ketones or ketimines of the formula Xa or Xb $$\underset{R^2}{\overset{R^1}{>}}=O, \quad (Xa)$$

$$\underset{R^2}{\overset{R^1}{>}}=NH \quad (Xb)$$

where $R^1$, $R^2$ are each alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl, or $R^1$ and $R^2$ together form $(CH_2)_l$—$CH_2$—X—$(CH_2)_m$ x is $CH_2$, $CHR^5$, oxygen (O), sulfur (S) or $NR^5$, $R^5$ is hydrogen (H), alkyl such as $C_{1-4}$-alkyl, alkylphenyl such as $C_{7-40}$-alkylphenyl, and I, m are an integer from 1 to 4 to form the corresponding secondary alcohols XIa or primary amines XIb $$\underset{R^2}{\overset{R^1}{>}}\underset{H}{C}-OH \quad (XIa)$$

$$\underset{R^2}{\overset{R^1}{>}}\underset{H}{C}-NH_2. \quad (XIb)$$

The substituents $R^1$ to $R^5$, the variable X and the indices l, m in the compounds I, II, III, IV, V, VI, VII, VIIIa, VIIIb, IXa, IXb, Xa, Xb, XIa and XIb independently have the following meanings:

$R^1, R^2, R^3, R^4$:

alkyl such as $C_{1-200}$-alkyl, preferably $C_{1-20}$-alkyl, particularly preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly $C_{1-4}$-alkyl, and also preferably $C_{40-200}$-alkyl such as polybutyl, polyisobutyl, polypropyl, polyisopropyl and polyethyl, particularly preferably polybutyl and polyisobutyl, cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl, hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl) ethyl, aminoalkyl such as $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl) aminomethyl, hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl and 3-(2-hydroxyethylamino)propyl, alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_{2-4}$-alkoxyalkyl, dialkylaminoalkyl such as $C_{3-30}$-dialkylaminoalkyl, preferably $C_{3-20}$-dialkylaminoalkyl, particularly preferably $C_{3-10}$-N,N-dialkylaminoalkyl such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino) ethyl and 2-(N,N-diisopropylamino)ethyl, 3-(N,N-dimethylamino)propyl, $(R^5)_2N-(CH_2)_l$, alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylaminoethyl, ethylaminomethyl, 2-ethylaminoethyl and 2-(isopropylamino)ethyl, $(R^5)HN-(CH_2)_q$, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, heteroaryl such as 2-pyridinyl, 3-pyridinyl, 4-pyridinyl, pyrazinyl, pyrrol-3-yl, imidazol-2-yl, 2-furanyl and 3-furanyl, aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, heteroarylalkyl such as $C_{4-20}$-heteroarylalkyl, e.g. pyrid-2-yl-methyl, furan-2-yl-methyl, pyrrol-3-yl-methyl and imidazol-2-yl-methyl, alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, alkylheteroaryl such as $C_{4-20}$-alkylheteroaryl, e.g. 2-methyl-3-pyridinyl, 4,5-dimethyl-imidazol-2-yl, 3-methyl-2-furanyl and 5-methyl-2-pyrazinyl, in the case of unsaturated compounds of the fomula I, Xa and Xb, $R^1$ and $R^2$ may also together form a $-(CH_2)_l-X-(CH_2)_m-$ group such as, $-(CH_2)_4-$, $-(CH_2)_5-$, $-(CH_2)_6-$, $-(CH_2)_7-$, $-(CH_2)-O-(CH_2)_2-$, $-(CH_2)-NR^5-(CH_2)_2-$, $-(CH_2)-CHR^5-(CH_2)_2-$, $-(CH_2)_2-O-(CH_2)_2-$, $-(CH_2)_2-NR^5-(CH_2)_2-$, $-(CH_2)_2-CHR^5-(CH_2)_2-$, $-CH_2-O-(CH_2)_3-$, $-CH_2-NR^5-(CH_2)_3-$, or in the case of unsaturated compounds of the formula I, $R^2$ and $R^4$ may also together form a $-(CH_2)_l-X-(CH_2)_m-$ group such as $(CH_2)_2-(CH_2)_4-$, $-(CH_2)_5-$, $-(CH_2)_5-$, $-(CH_2)_6-$, $-(CH_2)_7-$, $-(CH_2)-O-(CH_2)_2-$, $-(CH_2)-NR^5-(CH_2)_2-$, $-(CH_2)-CHR^5-(CH_2)_2-$, $-(CH_2)_2-O-(CH_2)_2-$, $-(CH_2)_2-NR^5-(CH_2)_2-$, $-(CH_2)_2-CHR^5-(CH_2)_2-$, $-CH_2-O-(CH_2)_3-$, $-CH_2-NR^5-(CH_2)_3-$, $R^5$:

hydrogen (H), alkyl, preferably $C_{1-4}$-alkyl such as methyl, ethyl, n-propyl, isopropyl, n-butyl, isobutyl, sec-butyl and tert-butyl, preferably methyl and ethyl, particularly preferably methyl, alkylphenyl, preferably $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl,

X:

$CH_2$, $CHR^5$, oxygen (O), sulfur (S) or $NR^5$, preferably $CH_2$ and O, l:

an integer from 1 to 4 (1, 2, 3 or 4), preferably 1 and 2, m:

an integer from 1 to 4 (1, 2, 3 or 4), preferably 1 and 2.

Organic compounds having aliphatically unsaturated groups which can be used in the process of the present invention include virtually all compounds having one or more aliphatic (i.e. nonaromatic) unsaturated CC or CN or CO bonds, i.e. aliphatic CC double bonds or CC triple bonds (e.g. olefinic or acetylenic CC bonds), aliphatic CN double bonds or CN triple bonds (e.g. imine groups or nitrile groups) and aliphatic CC double bonds (e.g. aldehyde groups or keto groups). The unsaturated organic compounds can be linear, branched or cyclic. There are virtually no restrictions on the number of carbon atoms in the compounds to be hydrogenated. Furthermore, the unsaturated organic compounds may bear substituents or contain functional groups which are inert under the conditions of the hydrogenation, for example hydroxyl, alkoxy, alkylamino or dialkylamino groups, or are also hydrogenated under the conditions.

If compounds containing a CC or CN triple bond, e.g. alkynes or nitriles, or compounds having two or more aliphatically unsaturated groups, e.g. dienes, allenes, polyenes, polyynes, alkynenes, enals, enones, enimines, are to be hydrogenated, corresponding monohydrogenated, dihydrogenated or polyhydrogenated products can be obtained in each case as a function of the reaction conditions chosen.

For example, preference is given to hydrogenating the following organic compounds having aliphatically unsaturated groups:

alkenes and alkynes such as ethylene (to ethane), acetylene (to ethylene and/or ethane), propene (to propane), propyne (to propene and/or propane), propadiene (to propene and/or propane), 1-butene (to n-butane), 2-butene (to n-butane), 1-butyne (to 1-butene and/or n-butane), 2-butyne (to 2-butene and/or n-butane), vinylacetylene (to 1,3-butadiene), 1,3-butadiene (to 1 butene and/or n-butane), 1,2-butadiene (to 1-butene and/or n-butane), cyclopentene (to cyclopentane), 1,3-cyclopentadiene (to cyclopentene and/or cyclopentane), 1,4-pentadiene (to 1-pentene and/or n-pentane), cyclohexene (to cyclohexane), 1-vinyl-3-cyclohexene (to 1-vinylcyclohexane and/or ethylcyclohexane), polyisobutene, phenylalkenes and phenylalkynes, e.g. styrene (to ethylbenzene), phenylacetylene (to styrene and/or ethylbenzene), alkenols and alkynols, e.g. 2-butene-1,4-diol (to butane-1,4-diol), 2-butyne-1,4-diol (to cis-2-butene-1,4-diol and/or butane-1,4-diol), alkenals such as 2-ethylhexene-2-al (to 2-ethylhexanol), aldehydes such as hydroxypivalaidehyde (to neopentyl glycol), 3-methylpent-1-en-3-al (to 3-methypentanol-3), imines such as isophorone nitrilimine (IPNI) (to isophorondiamine (IPDA)), nitriles such as 3-dimethylaminopropionitrile (to 3-(dimethylamino)propylamine), 3-diethylaminopropionitrile (to 3-diethylaminopropylamine), 3-aminopropionitrile (to 1,3-diaminopropane), bis(2-cyanoethyl)amine (to dipropylenetriamine), N-(2-cyanoethyl)ethylenediamine (to N-(3-aminopropyl)ethylenediamine), N,N'-di(2-cyanoethyl)ethylenediamine (to N,N'-di(3-aminopropyl(ethylenediamine), adiponitrile (to hexamethylenediamine), isophoronenitrile (IPN) (to isophoronediamine), 3-hydroxypropionitrile (to 3-amino-1-propanol), N-(2-cyanoethyl)morpholine (to N-(3-aminopropyl)morpholine), N-(2-cyanoethyl) caprolacta (to 1,8-diazabicyclo[5.4.0]undec-7-ene), isophthalonitrile (to metaxylylenediamine), mixture of adiponitrile and dimethylamine in a molar ratio of 1:$\geq$2 (to N,N,N',N'-tetramethylhexamethylenediamine), mixture of 3-N-methylaminopropionitrile and monomethylamine in a molar ratio of 1:$\geq$1 (to N, N'-dimethylpropylenediamine), mixture of 3-(dimethylamino)propionitrile and 3-(dimethylamino)propylamine (DMAPA) in a molar ratio of 1:$\geq$1 (to bis-[((3-dimethylamino)propyl]amine (bis-DMAPA)).

As can be seen from the last three examples, the process of the present invention can also be employed for preparing a secondary amine by reaction of a nitrile with a primary amine in the presence of hydrogen and for preparing a tertiary amine by reaction of a nitrile with a secondary amine in the presence of hydrogen. Preferred nitrites are dinitriles and nitrites of the formula VI. Amines which are preferably used are monomethylamine, monoethylamine, dimethylamine and diethylamine. Such amine syntheses are known, for example, from EP-A1-691 157 (BASF AG); a person skilled in the art may find further process details in this European patent publication.

The hydrogenation process of the present invention is generally carried out continuously or batchwise in a manner similar to or exactly like the known heterogeneously catalyzed hydrogenation processes employed for the same purposes. The catalyst is preferably installed as a fixed bed in the reactor (e.g. downflow mode or upflow mode). However, the hydrogenation can also be carried out as a fluidized-bed reaction with upward and downward swirling motion of catalyst material.

The hydrogenation process of the present invention can be carried out as a heterogeneously catalyzed gas-phase process in which both the starting material (i.e. the unsaturated organic compound) and the hydrogenation hydrogen are present in the gas phase, or as a heterogeneously catalyzed gas-/liquid-phase process in which at least part of the starting material is present in the liquid phase and hydrogen is present in the gas phase and/or in dissolved form in the liquid phase. The parameters such as space viscosity over the catalyst, temperature and pressure are chosen in a manner analogous to the known processes. The temperature is usually in the range from 20° C. to 300° C., in particular from 40° C. to 180° C., and the absolute pressure is in the range from 1 to 320 bar, in particular from 30 to 250 bar, (gas-/liquid-phase process) or in the range from 1 to 100 bar, in particular from 5 to 80 bar (gas-phase process).

In the gas-/liquid-phase process, the staring materials may, if desired, be diluted with a suitable solvent such as tetrahydrofuran, dioxane, N-methylpyrrolidone or ethylene glycol dimethyl ether.

The amount of hydrogen used, based on the amount of starting material to be hydrogenated, is generally dependent on the quantity of CC, CN and CO double bonds and CC and CN triple bonds to be hydrogenated in the starting material. In general, the hydrogen is used in an amount ranging from 0.8 times to 5 times the stoichiometrically required amount for complete reaction of the hydrogen on a single pass through the reactor, preferably in the range from 0.95 times to 2 times this amount. The hydrogenation of triple bonds normally proceeds more quickly than that of conjugated double bonds, and these are in turn hydrogenated more quickly than unconjugated double bonds. This makes it possible for the process to be controlled appropriately by means of the amount of hydrogen added. It is also possible to use a higher excess of hydrogen, for example a ten-fold excess of hydrogen. The hydrogen can contain inerts, for example noble gases such as helium, neon or argon, other inert gases such as nitrogen, carbon dioxide and/or lower alkanes, e.g. methane, ethane, propane and/or butane. Such inert gases in the hydrogen are preferably present in a concentration of less than 30% by volume. The hydrogen is preferably free of carbon monoxide.

The process can be carried out continuously in one or more reactors connected in parallel or in series, in each case in a single pass or in the recycle mode. When the process is carried out in the gas/liquid phase, the feed stream is, after it has passed through a reactor, usually freed of gases in a separator and part of the liquid obtained is returned to the reactor. The ratio of recirculated feed stream and fresh feed fed into the reactor, viz. the recirculation ratio, is set so that the desired conversion is achieved under the prevailing reaction conditions, e.g. pressure, temperature, throughput and amount of hydrogen.

If the catalyst is present as a fixed bed, it can be advantageous in terms of the selectivity of the reaction for the shaped catalyst bodies in the reactor to be mixed with inert shaped catalyst bodies so as to "dilute" them. The proportion of inert shaped bodies in such catalyst beds can be from 20 to 80% by volume, preferably from 30 to 60% by volume and in particular from 40 to 50% by volume.

After the reaction product mixture has advantageously been depressurized, the hydrogenation products obtained are purified by, for example, distillation or rectification, liquid extraction or crystallization. Excess hydrogen is advantageously returned to the reaction zone. The same applies to any incompletely reacted starting material.

The products of catalytic hydrogenation prepared using the process of the present invention are, for example, important intermediates in the chemical industry, for example, the 1,4-butanediol prepared in this way from 2-butene-1,4-diol and 2-butyne-1,4-diol.

EXAMPLES

Preparation of Catalysts

Catalyst A (According to the Present Invention):

Catalyst A was prepared as follows by precipitation of the components Cu, Co and Ni onto monoclinic zirconium dioxide which has been initially placed in the precipitation vessel:

A suspension of 155 g of monoclinic zirconium dioxide powder (BET=105 m$^2$ g$^{-1}$) in 2 l of water was placed in a stirrable glass vessel and heated to 70° C. while stirring. A solution of 190.1 g of Cu(NO$_3$)$_2$×2.5 H$_2$O, 561.9 g of Ni(NO$_3$)$_2$×6 H$_2$O and 543.7 g of Co(NO$_3$)$_2$×6 H$_2$O in 2.8 l of water was then added dropwise over a period of 30 minutes. The pH was kept constant at 6.0 by simultaneous dropwise addition of a 20% strength sodium carbonate solution (700 g of Na$_2$CO$_3$ in 2.8 l of water). After addition of the solutions, the mixture was stirred at 70° C. for another 1 hour and the pH was finally increased to 7.4 by addition of sodium carbonate solution. The suspension was pumped onto a suction filter and washed with 100 l of water. The filter cake was dried at 200° C. in a drying oven for 16 hours, subsequently comminuted to a particle size of <1.6 mm and calcined at 400° C. in a stream of air (150/h) in a rotary tube furnace for 2 hours.

The catalyst powder obtained in this way had the composition:

28% by weight of Ni, calculated as NiO,
28% by weight of Co, calculated as CoO,
11% by weight of Cu, calculated as CuO, and
33% by weight of Zr, calculated as ZrO$_2$.

The powder was admixed with 3% by weight of graphite, compacted, once again comminuted to <1.6 mm and finally pressed to form 4.75×3 mm pellets. The pellets were then calcined at 400° C. in air in a muffle furnace for 2 hours. The pellets were then reduced in a stream of hydrogen and nitrogen in a reduction column, firstly at 150° C. for 6 hours and then at 280° C. for 6 hours. After cooling to room temperature, the pellets were passivated in a stream of diluted air.

Catalyst B (Comparative Catalyst):

The comparative catalyst was prepared in the same way as the catalyst A according to the present invention, except that no monoclinic zirconium dioxide was initially placed in the precipitation vessel. Instead, 775 g of a zirconium acetate solution having a concentration of 20% by weight, calculated as ZrO$_2$, (based on the weight of the zirconium acetate solution) was added to the metal salt solution comprising copper, cobalt and nickel nitrates (coprecipitation). The further preparation was analogous to that of catalyst A. The catalyst powder obtained analogously had the same composition as that described for catalyst A.

Example 1

To test the mechanical stability of the catalysts A and B under the hydrogenative reaction conditions of the hydrogenative amination of hydroformylated polyisobutene (PIB-Oxo; molar mass: 1000) to the primary amine PIBA according to the reaction equation

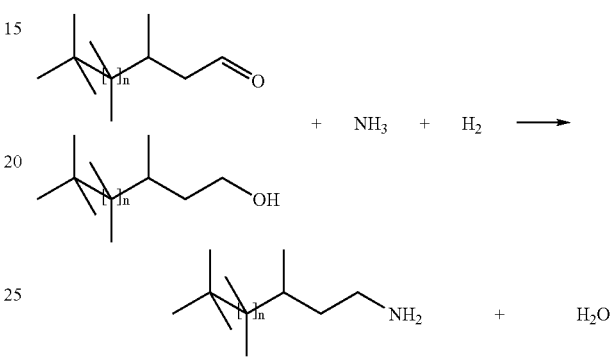

the catalysts were subjected to a boiling test in an autoclave (autoclave test) in which the reaction conditions were set as follows:

20 g of catalyst were placed in a wire basket in a stirring autoclave. 150 ml of a PIBA/Mihagol (50/50) solution were added thereto, so that the catalyst pellets were well covered with liquid. The autoclave was closed, flushed with nitrogen, the stirrer was set to a speed of 700 rpm, 50 bar of H$_2$ were injected and the contents of the autoclave were heated to 200° C. The pressure was then set to 200 bar by additional injection of H$_2$. Under these conditions, the catalyst was treated for different periods of time. The autoclave was subsequently cooled, carefully depressurized and the mechanical stability of the catalyst was determined by measuring the lateral compressive strength (LCS).

For this purpose, the catalyst pellet was subjected to an increasing force on the cylindrical surface between two parallel plates until fracture occurred. The force recorded on fracture is the lateral compressive strength. The determination was carried out on a test apparatus from Zwick, Ulm, having a fixed rotating plate and a freely movable, vertical punch which pressed the shaped body against the fixed rotating plate. The freely movable punch was connected to a load cell to measure the force. The instrument was controlled by a computer which recorded and evaluated the measured values. 25 intact pellets (i.e. pellets which were crack-free and had no broken edges) were taken from a well mixed catalyst sample, their lateral compressive strength was determined and subsequently averaged.

In the accompanying FIG. 1, the lateral compressive strengths (unit: Newton, N) of the two catalysts A and B are plotted over the time of the autoclave test (in hours):

In the case of the catalyst B prepared by coprecipitation, the X-ray diffraction pattern after the boiling test indicated that the initially X-ray-amorphous ZrO$_2$ phase had been converted into tetragonal and monoclinic ZrO$_2$. In the case of catalyst A, no recrystallization (=change of modification) was found.

We claim:

1. A process forte catalytic hydrogenation of a non-aromatic group in an organic compound in the presence of a catalyst whose preparation has involved precipitation of catalytically active components onto monoclinic, tetragonal or cubic zirconium dioxide, and wherein the catalytically active components of the catalyst before treatment with hydrogen comprise from 20 to 65% by weight of oxygen-containing compounds of zirconium, calculated as $ZrO_2$, from 1 to 30% by weight of oxygen-containing compounds of copper, calculated as CuO, from 15 to 50% by weight of oxygen-containing compounds of nickel, calculated as NiO, and from 15 to 50% by weight of oxygen-containing compounds of cobalt, calculated as CoO.

2. A process as claimed in claim 1, wherein the catalytically active components precipitated further comprise metal salts of an additional metal selected from transition groups VIII and IB of the Periodic Table.

3. A process as claimed in claim 2, wherein the metal salts are basic salts which are sparingly soluble or insoluble in water.

4. A process as claimed in claim 2, wherein the salts are oxides, hydrated oxides, hydroxides, carbonates and/or hydrogencarbonates.

5. A process as claimed in claim 2, wherein the additional metal is selected from the group consisting of Fe, Ru, Rh, Pd and Pt.

6. A process as claimed in claim 1, wherein a molar ratio of nickel to copper is greater than 1.

7. A process as claimed in claim 1, wherein the monoclinic, tetragonal or cubic zirconium dioxide contains one or more oxides of metals of transition groups IIIB or main group IIA of the Periodic Table.

8. A process as claimed in claim 1, wherein the hydrogenation is carried out at from 20 to 300° C.

9. A process as claimed in claim 1, wherein the hydrogenation is cried out in the gas/liquid phase at absolute pressures of from 1 to 320 bar or in the gas phase at pressures of from 1 to 100 bar.

10. A process as claimed in claim 1, wherein the unsaturated group is an aliphatic CC double bond or CN double bond.

11. A process as claimed in claim 1, wherein the unsaturated group is an aliphatic CC triple bond or CN triple bond.

12. A process as claimed in claim 1, wherein the aliphatically unsaturated group is an aldehyde group or keto group.

13. A process as claimed in claim 1 for preparing a secondary amine, wherein the aliphatically unsaturated group is a nitrile group and a reaction with a primary amine is carried out.

14. A process as claimed in claim 1 for preparing a tertiary amine, wherein the aliphatically unsaturated group is a nitrile group and a reaction with a secondary amine is carried out.

15. A process as claimed in claim 1 wherein the non-aromatic group in the organic compound is an aliphatically unsaturated group.

* * * * *

UNITED STATES PATENT AND TRADEMARK OFFICE
CERTIFICATE OF CORRECTION

PATENT NO. : 7,122,702 B2
APPLICATION NO. : 10/731167
DATED : October 17, 2006
INVENTOR(S) : Gerlach et al.

It is certified that error appears in the above-identified patent and that said Letters Patent is hereby corrected as shown below:

Claim 1, column 13, line 2: "forte" should read --for the--

Signed and Sealed this

First Day of May, 2007

JON W. DUDAS
*Director of the United States Patent and Trademark Office*